United States Patent [19]

Richards

[11] 4,346,701
[45] Aug. 31, 1982

[54] GAS ADMINISTRATION APPARATUS

[75] Inventor: David J. Richards, Bradford, England

[73] Assignee: The Medishield Corporation Limited, London, England

[21] Appl. No.: 134,803

[22] Filed: Mar. 28, 1980

[51] Int. Cl.³ .......................................... A61M 11/00
[52] U.S. Cl. .......................... 128/200.14; 128/200.19; 74/483 K; 251/149.9; 137/637.1; 137/614.06
[58] Field of Search ...................... 128/200.11, 200.14, 128/200.16, 200.17, 200.19, 200.21, 203.12, 203.14, 203.25, 203.28, 204.13, 204.14; 261/DIG. 65; 74/483 R, 483 K; 251/111, 113, 114, 149.9 X; 137/637.1, 614.06

[56] References Cited

U.S. PATENT DOCUMENTS

| | | | |
|---|---|---|---|
| Re. 27,364 | 5/1972 | German | 137/614.06 X |
| 1,340,930 | 5/1920 | Catlin | 74/483 R X |
| 2,185,061 | 12/1939 | Meyers | 137/637.1 |
| 2,646,474 | 7/1953 | Stration | 74/483 R X |
| 2,756,612 | 7/1956 | Schleicher | 74/483 R X |
| 2,764,182 | 9/1956 | Mitcham | 74/483 R X |
| 3,021,840 | 2/1962 | Hallamore et al. | 128/204.14 |
| 3,034,544 | 5/1962 | Griswold | 137/614.06 X |
| 3,703,172 | 11/1972 | Hay | 128/200.13 |
| 3,831,599 | 8/1974 | Needham | 128/203.12 |
| 4,058,120 | 11/1977 | Caparrelli et al. | 128/203.12 |
| 4,246,115 | 1/1981 | Swank | 74/483 K |

FOREIGN PATENT DOCUMENTS

| | | | |
|---|---|---|---|
| 788103 | 12/1957 | United Kingdom | 128/200.19 |
| 1193522 | 6/1970 | United Kingdom | 128/200.19 |
| 1217144 | 12/1970 | United Kingdom | 128/204.26 |
| 1491807 | 11/1977 | United Kingdom | 128/200.19 |

OTHER PUBLICATIONS

Ohio, Unitrol Anesthesia Machine, Airco Products Catalog Form No. 9906 (Rev. 1978).

Primary Examiner—Henry J. Recla
Attorney, Agent, or Firm—Roger M. Rathbun; Larry R. Cassett

[57] ABSTRACT

A gas flow unit such as a vaporizer, mountable on a gas administration apparatus such as an anaesthesia machine in plug-in fashion includes an interlock system which prevents a valve for controlling the admission to the unit of gas from a supply provided by the apparatus from being operated before a locking mechanism has locked the unit to the anaesthesia machine.

The interlock system also includes actuating means which when the unit is mounted on the anaesthesia machine, opens respective valve members in ports located on the anaestheia machine only when the control valve is moved to its operating position.

In the case when two similar units are mounted side-by-side on the anaesthesia machine and intended for use as alternatives, the interlock system includes pins which when the control valve on one unit is moved to its operating position, extend outwardly from the unit to prevent the control valve on the other unit from being operated.

7 Claims, 8 Drawing Figures

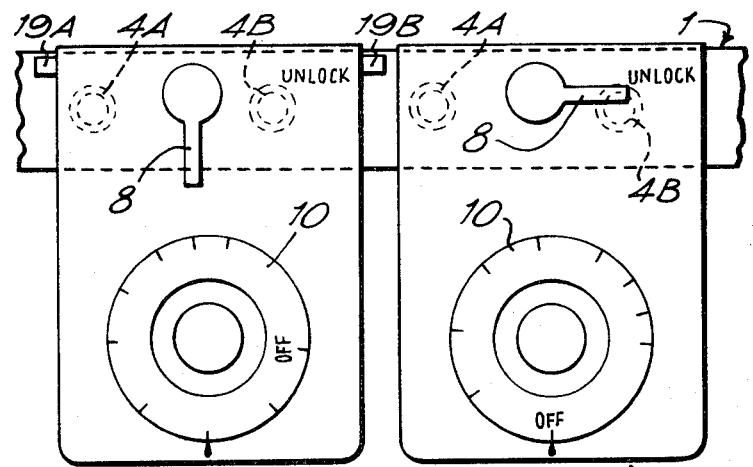
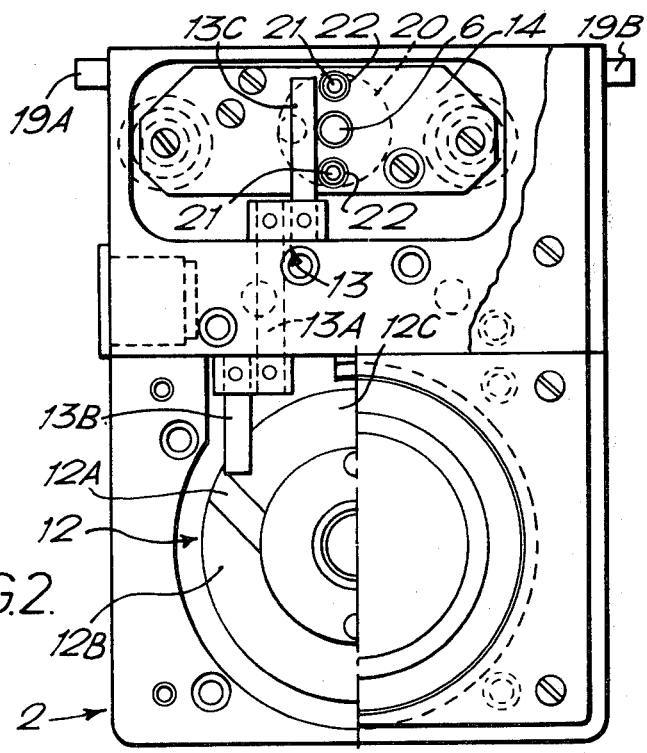

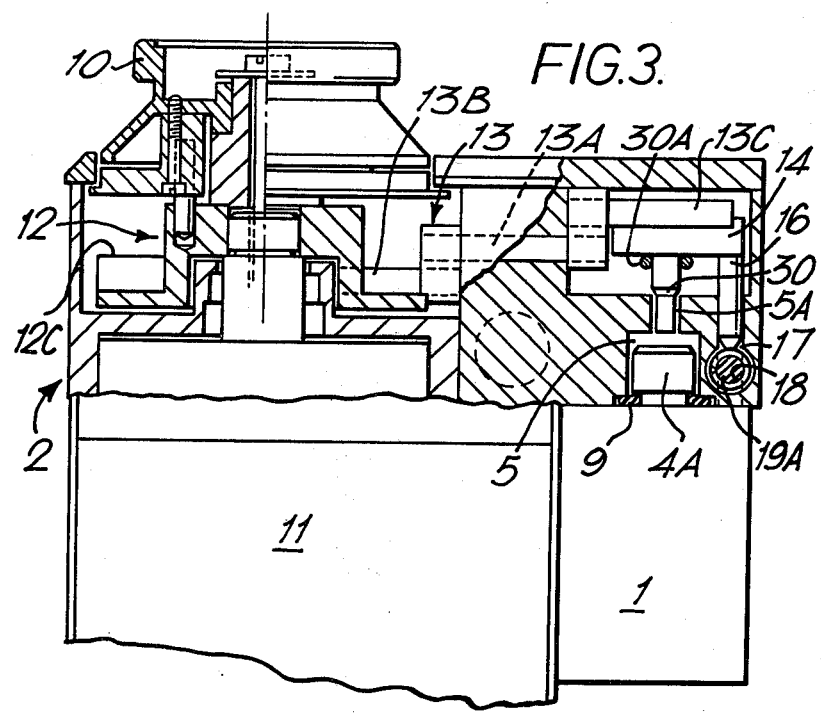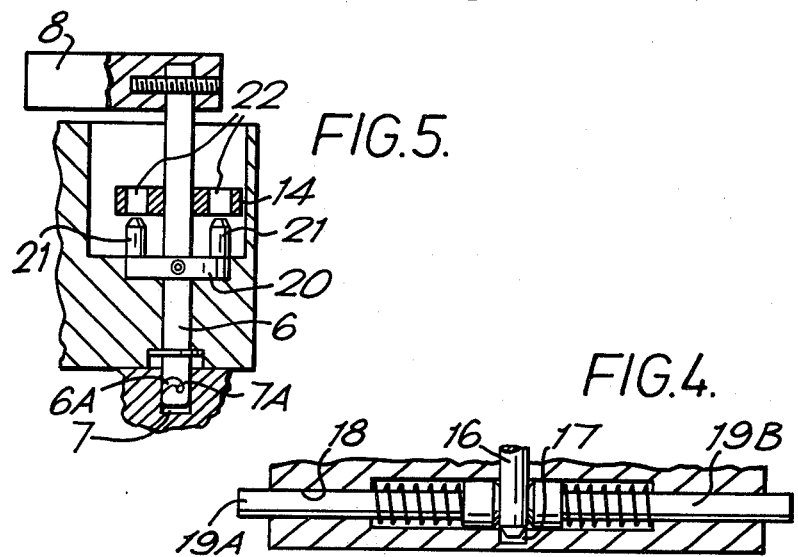

GAS ADMINISTRATION APPARATUS

BACKGROUND

The present invention relates to gas-flow units which are adapted to be mounted on gas-administration apparatus and in particular, to gas-flow units such as vaporisers which are adapted to be mounted on apparatus for the administration of gaseous anaesthetics or analgesics (which, for convenience, will hereinafter be referred to collectively as "anaesthetics") or other "medical" gases or gas mixtures such as oxygen or air.

For the purposes of this specification the term "gas-flow unit" is intended to embrace any type of unit which is mountable on a gas-administration apparatus and adapted to receive a gas supply during the operation of the apparatus "Gas-flow units" therefore comprise, inter alia vaporisers, flow meters, gas mixers, volume meters, ventilators, pressure gauges and absorbers.

In United Kingdom patent specification No. 1,385,670 there is described a gas-administration apparatus on which one or more gas-flow units can be mounted in a removable, plug-in fashion. A plug-in system of this nature simplifies the installation and removal of gas-flow units from the apparatus, so facilitating maintenance and cleaning of the units, as also the replacement of a unit should it fail during an operation. Furthermore, this system is of great value to the anaesthetist in allowing him to change the unit(s), for example, vaporiser(s) installed on a given anaesthesia apparatus both easily and quickly. In this way the apparatus can readily be adapted for the administration of any one (or more) of the wide range of volatile anaesthetic agents currently available and the anaesthetist can accordingly ensure that the correct agent is made available for the needs of every patient.

Known gas-flow units adapted for the aforesaid 'plug-in' type of system usually include a locking mechanism or member which cooperates with a backbar or rack of the anaesthesia apparatus to physically lock the unit in place when installed. Operation of the lock may also be effective to pull the unit tightly against seals provided around the cooperating ports which are provided on the anaesthesia apparatus to effect the desired gas supply to the unit. However, it is possible to install a known unit of this type and thereafter operate the apparatus without the lock having been moved into its operative position. The installed but unlocked gas-flow unit may thereby be inadvertently displaced or in any event gas leakage may occur past the seals which have not been compressed by operation of the lock and which are therefore not fully effective.

SUMMARY OF THE INVENTION

According to the present invention, a gas-flow unit adapted to be mounted on a gas-administration apparatus in a removable plug-in fashion, comprises means for controlling the admission to the unit of gas from a supply provided by the apparatus, a locking mechanism for cooperation with the apparatus to lock the unit in place when mounted on the apparatus, and an interlock system in which the manipulation of the control means into an operating position which provides for the admission of gas from the apparatus to the unit is prevented unless the locking mechanism has been moved into a position in which it is adapted to lock the unit on the apparatus.

It is thereby ensured that the unit cannot be switched into the gas circuit unless it is properly locked in place on the apparatus, and in the event of a gas-flow unit being installed but not locked in place this will become immediately apparent to the operator by his inability to manipulate the unit's control means.

The ports of known 'plug-in' type anaesthesia apparatus which are adapted to effect the supply of gas to the removable gas-flow units usually embody spring-biased valve members which, when a cooperating gas-flow unit is not installed, seal off the respective ports from communication with the atmosphere but which, when a cooperating unit is installed, are moved away from the port-closing position by abutment with actuating members of the unit to provide fluid communication between the ports and the unit. So long as the gas-flow unit remains in place on the apparatus the corresponding port valves will be open, even though the control means of the unit may be in the OFF position. Thus, even though it is not intended that the gas-flow unit be switched into the gas circuit, residual gas or vapour which exists within the internal passages of the unit between the aforesaid ports and control means may find its way into the circuit. Further, if the gas-flow unit is a vaporiser and its control means is a valve which does not seal perfectly when in the OFF position, significant amounts of unwanted vapour may be delivered into the circuit, unknown to the anaesthetist.

Clearly, such a state of affairs is undesirable and in a preferred embodiment of the invention, we seek to eliminate these problems.

In a preferred embodiment, the control means controls the admission to the unit of gas from a supply provided through one or more cooperating ports on the apparatus, the or each port having a valve member normally urged into a position in which it acts to close the respective port, and the unit including actuating means forming part of the interlock system such that when the unit is mounted on the apparatus, the actuating means is effective to move the respective valve member of the or each cooperating port away from the port closing position only when the control means has been manipulated to its operating position.

It is common practice for an anaesthesia apparatus to have mounted on it two separate vaporisers for delivering different volatile anaesthetic agents to a carrier gas, so that the same basic anaesthesia apparatus can be used during a series of surgical operations wherein the needs of different patients require the use of the different agents. In such a case it is clearly undesirable to run the risk of the two agents being delivered to a patient at the same time or otherwise becoming mixed. Apart from the case of alternative vaporisers, however, there may be other cases where it is desirable for an anaesthesia apparatus or other gas-administration apparatus to include two or more alternative units which again should not be used at the same time. For example, there can be mentioned an apparatus which incorporates two units, eg. flow meters which are designed to operate with different ranges of gas flow rates or apparatus which includes both a trichlorethylene vaporiser and a soda lime absorber for $CO_2$ (which an anaesthetist may wish to use during different operations but which must not be used together as trichlorethylene can react with soda lime to produce a toxic gas).

Known anaesthesia apparatus which provide for 'multiple choice' vaporisers typically include the backbar or rack, previously mentioned, upon which the vaporisers are mounted and which provides the necessary pipework or ducting to enable each vaporiser to be connected into the gas circuit. In an effort to prevent the possibility of cross-contamination of the different vapours it is known to provide a selector valve whereby the carrier gas can only be supplied to one selected vaporiser at any one time. This system has the disadvantage, however, that two valves must be operated to bring any one vaporiser into the circuit, ie. the selector valve on the backbar and the control valve on the vaporiser which permits the passage of the carrier gas through the vaporiser and controls the concentration of the vaporised agent delivered to the carrier gas. Furthermore, this system can still permit a situation to arise where, through incorrect manipulation of the valves, either the wrong agent, or the wrong concentration of the correct agent, or no agent at all, is delivered to the patient without the anaesthetist immediately being aware of the fact.

In the preferred embodiment of the invention we seek to eliminate or at least reduce the problems associated with the use of a selector valve in a 'multiple choice' anaesthesia apparatus whilst still ensuring that only a selected one of two or more alternative vaporisers can be connected into the gas circuit at any one time.

In the preferred embodiment, the interlock system includes at least one pin extendible outwardly from the unit on manipulation of the control means to its operating position to prevent the control means of a similar adjacent unit mounted on the apparatus from being manipulated to its operating position.

An embodiment of the invention will now be described, by way of example, reference being made to the Figures of the accompanying diagrammatic drawings, in which:

DESCRIPTION OF DRAWINGS

FIG. 1 is a schematic plan view of two alternative gas-flow units (vaporisers) mounted on the backbar or an anaesthesia apparatus;

FIG. 2 is a more detailed plan view of one of the vaporisers of FIG. 1, with certain parts broken away;

FIG. 3 is an elevation of the vaporiser of FIG. 2, partly in vertical section;

FIGS. 4, 5 and 6 are respective detail sectional views of the vaporiser of FIGS. 2 and 3.

DESCRIPTION OF PREFERRED EMBODIMENT

Figure 6:
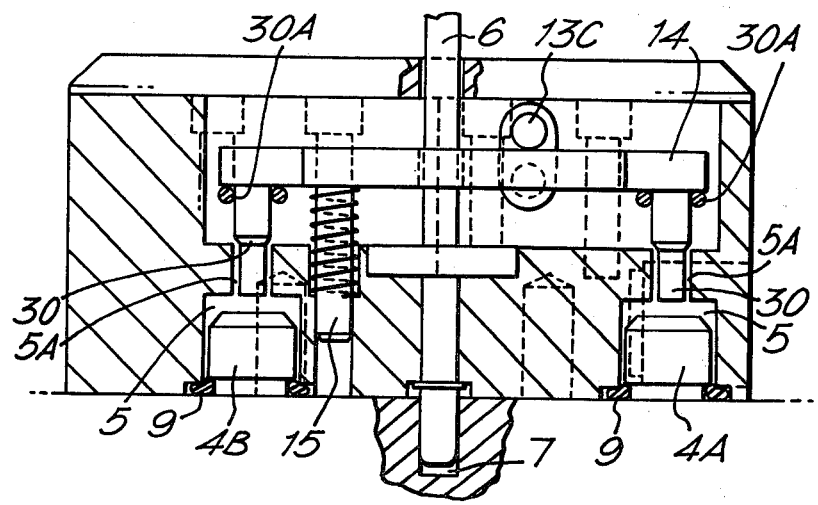

Referring to the drawings, in FIG. 1 there is shown the back bar 1 of an anaesthesia apparatus upon which two gas-flow units in the form of vaporisers 2 and 3 adapted to deliver different volatile anaesthetic agents, are mounted side-by-side. The vaporisers are installed in a removable, plug-in fashion, being located on the back bar by respective pairs of ports 4a,4b, upstanding from the back bar and which are received in corresponding recesses 5 in the rear portions of the vaporisers (see also FIGS. 3 and 6).

Means are provided for locking each vaporiser in place on the back bar, comprising a rotatable shaft 6 borne by the vaporiser and which extends into a recess 7 in the back bar when the vaporiser is lowered onto the ports 4a,4b. The shaft has a profiled groove 6a (FIG. 5) which engages with a latching member 7a in the recess 7 when the shaft is turned by a thumb-lever 8 through 90°, from the position indicated for the vaporiser 3 in FIG. 1 to the position indicated for the vaporiser 2. Operation of the lock is effective to prevent the vaporiser being displaced from the back bar and also serves to draw the rear portion of the vaporiser tightly down against the backbar, thereby ensuring a gas-tight fit against annular seals 9 provided around the bases of the ports 4a, 4b. It is to be noted that the thumb-lever 8 of vaporiser 3 is shown in the unlocked position in FIG. 1 for the purposes of illustration only, as it is intended that so long as a vaporiser remains in place on the back bar its lock will be in operation. Indeed, as will be more fully described hereinafter, it is impossible to switch such a vaporiser into the gas circuit unless it is locked to the backbar.

Mounted on the top of each vaporiser is means for controlling the admission to the vaporiser of gas including a concentration dial 10 linked to a rotary plate or other suitable form of control valve located within the body of the vaporiser. It is assumed that each vaporiser is of the by-pass type, as described for example in United Kingdom patent specification No. 1 224 478, having a vaporising chamber in the lower portion 11 of the unit (FIG. 3) and a circuit by-passing the vaporising chamber. In use the carrier gas admitted to the vaporiser splits into two flows, one passing through the vaporising chamber and the other through the by-pass circuit, the two flows thereafter reuniting before leaving the vaporiser. The detailed construction of the control valve will not be described herein, but briefly its function is to vary the relative proportions of the gas flows passing through the vaporising chamber and by-pass circuit in response to movement of the dial 10, thereby varying the concentration of vaporised anaesthetic agent in the outlet flow. The dial has a graduated scale to indicate the anaesthetic concentration set by the control valve, and also indicates an OFF position in which the control valve shuts off gas flow through the vaporiser.

Referring now to FIGS. 2 and 3, mounted beneath, and rotatable with, the concentration dial 10 is an annular cam 12 having an inclined shoulder 12a separating lower and upper flat steps 12b and 12c. Cooperating with this cam is a crank 13, borne centrally at 13a and its end portions 13b and 13c resting respectively on the surface of the cam 12 and the surface of a vertically reciprocable platform 14. The platform 14 is borne by a pair of spring-biased plungers 15 (of which one can be seen in FIG. 6) which urge the platform upwards against crank portion 13c which in turn urges the crank portion 13b downwards against the surface of cam 12. While the concentration dial 10 is in its OFF position (and the control valve is therefore closed) the crank portion 13b can rest upon the lower step 12b of the cam and the platform 14 is accordingly allowed to rise to its upper position as shown in FIG. 3. When, however, the concentration dial is moved (anti-clockwise) away from the OFF position to its operating position to thereby open the control valve the crank portion 13b has to rise up the shoulder 12a to the upper step 12c of the cam and in so doing the crank is rotated to the position indicated in FIG. 2, so that in turn the crank portion 13c pushes the platform 14 downwardly against its spring bias.

Depending from the rear of the platform 14 is a pin 16 reciprocable in a bore 17. Intersecting bore 17 is a bore 18 within which are housed a pair of pins 19a, 19b, spring-biased towards one another (see FIG. 4). So long as the platform 14 remains in its upper position the pin 16 is held clear of the bore 18 and the pins 19a and 19b remain wholly within the same. When, however, the platform is lowered by the action of turning dial 10 the pin 16 intrudes into the bore 18 and displaces the pins 19a and 19b to either side. In this condition the distal ends of the pins extend through the opposite ends of the bore 18, as shown in FIGS. 1,2 and 4 for vaporiser 2.

Thus it is seen that whenever the control valve of a vaporiser as described above is manipulated into a position which provides for the admission of gas to the vaporiser, the two pins 19a and 19b will extend, one to each side of the unit. Returning to FIG. 1 it is seen that the dial 10 of vaporiser 2 has been moved away from the OFF position to its operating position to open the associated control valve and accordingly its pins 19a, 19b are extended. If an attempt were now to be made to turn the dial of vaporiser 3 (assuming that its lock had already been operated), by virtue of the linkage comprising its cam 12, crank 13, platform 14 and pin 16 its own two pins 19a and 19b would likewise have to extend. However, the path of movement of its pin 19a is blocked by the pin 19b of vaporiser 2 and movement of its dial 10 is thereby prevented.

With this arrangement it will be understood that it is impossible to switch more than one of the vaporisers into the gas circuit at any one time, and the above described interlock system provided by the pins 19a and 19b will, of course, be equally effective between any two similar vaporisers (or other gas-flow units having a similar mechanism) occupying either of the two mounting stations defined by the pairs of backbar ports 4a and 4b.

As previously indicated, the vaporisers 2 and 3 each comprise a mechanism for preventing operation of the vaporiser unless it is locked in position on the back bar 1. This mechanism will now be described with reference to FIGS. 2 and 5.

Fast with the shaft 6, beneath the platform 14, is a circular plate 20 having two upstanding pins 21. When the shaft is rotated into the LOCK position, these pins 21 underly respective holes 22 in the platform 14, so that subsequent movement of the dial 10 such as to lower the platform is unimpeded. However, while the shaft 6 is in the UNLOCK position the pins 21 underly unapertured portions of the platform. Consequently in this condition lowering of the platform is prevented and the dial 10 thereby cannot be turned away from its OFF position.

A further feature of the illustrated embodiment is the means whereby the backbar ports 4a,4b associated with either vaporiser are opened only when the associated vaporiser control valve is opened. FIG. 7 indicates the porting arrangement at each back bar station. The ports 4a and 4b communicate with respective bores 23a and 23b in the backbar, bore 23a being connected to an inlet duct 24 from the carrier gas supply and bore 23b to an outlet duct 25. The two bores are joined by a bore 26. A piston-like valve member 27 and stem 28 is provided in each bore 23a, 23b, each biased upwardly by a spring 29.

Figure 7A:
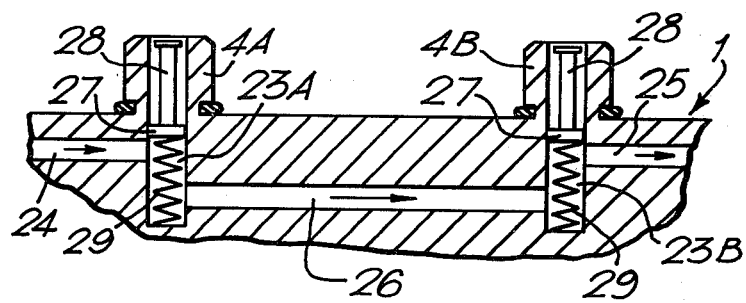
FIGS. 7A and 7B are schematic illustrations of the porting arrangement provided by the anaesthesia machine for each vaporiser, in two operative conditions.
Figure 7B:
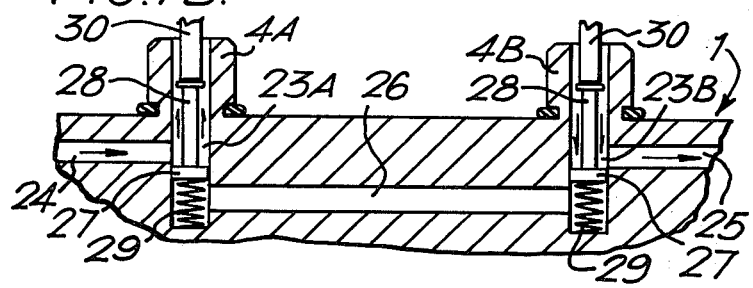

FIG. 7a shows the condition of the ports when no vaporiser is mounted at that station or when a vaporiser is mounted but not switched on. In this condition each port is closed and the inlet and outlet ducts 24 and 25 are connected together through bore 26. When a vaporiser is mounted at the station and its control valve is opened, however, the attendant lowering of the platform 14 brings respective actuating means in the form of pins 30 (FIGS. 3 and 6) down onto the valve stems 28 to move the valve members 27 into the positions indicated in FIG. 7b. In this condition port 4a is open to the inlet duct 24 and the port 4b is open to the outlet duct 25, the bore 26 being closed off. From port 4a the carrier gas enters the cooperating recess 5 of the vaporiser and passes through a side bore (not shown) from the recess into the body of the vaporiser to be split into two flows as hereinbefore described; (it will be noted that in this condition the top opening 5a from the recess will be closed by a seal 30a provided around the valve actuating pin 30). After the flows reunite the carrier gas/vapour mixture is fed to the other recess 5 of the vaporiser and thence passes through port 4b and into the outlet duct 25 of the backbar.

From the above it will be appreciated that while a vaporiser is mounted on the back bar, unless and until its dial 10 is moved away from the OFF position to open the associated control valve, the cooperating ports of the back bar are closed and the vaporiser is completely isolated from the gas circuit. Should any leakage of vapour from the vaporiser occur for any reason it can be vented from the recesses 5 through their top openings 5a (the pins 30 being withdrawn in this condition) and thence to the atmosphere through suitable further openings provided for the purpose.

Furthermore, while the vaporiser at either station is not switched on the corresponding ports 4a and 4b are by-passed by the carrier gas which enables a series connection of the two stations to the carrier gas supply to be effected. In other words, referring to FIGS. 7a and 7b, the outlet duct 25 from the illustrated station constitutes the inlet duct to the next station. By using a series connection of this type instead of the parallel connection which is more usual in anaesthesia machines providing for 'multiple choice' vaporisers, the amount of 'dead' pipework in the back bar can be minimised, thereby reducing the hazards associated with the build-up of explosive vapours such as ether in such pipework.

In a modification it is possible that the actuating pins 30 could be used to operate valves or mechanisms other than the valve members 37 which mechanisms might, for example, provide a connection to an indicator or pressure gauge which operates only when the control means is moved to its operating position.

I claim:

1. An anesthesia machine comprising a gas-administration apparatus, and a gas flow unit removably mounted on said gas administration apparatus in a plug-in fashion, said gas flow unit having control means to control the flow of gas to said gas flow unit from said gas-administration apparatus, at least one gas port in said gas-administration apparatus to conduct gas to said gas flow unit, locking means movable between a lock position wherein said gas flow unit is secured to said gas-administration apparatus and an unlock position, and interlock means cooperating with said locking means, said interlock means preventing said control means from allowing flow of gas from said gas-administration apparatus to said gas flow unit unless said locking means is in its lock position, valve means in said at least one port normally closing each of said at least one port, said gas flow unit further including actuating means to move said valve means to open said at least one port only when said locking means is in its lock position.

2. An anesthesia machine as defined in claim 1 comprising a plurality of gas flow units mounted on said gas-administration apparatus, said interlock means including two spring biased pins extending from opposite sides of each of said units and movable to an extended position against spring bias when one of said control means is moved to its open position, said control means of both gas flow units including a rotatable dial controlling the flow of gas through said gas flow unit, cam means movable with said rotatable dial, a crank having one end thereof bearing against said cam surface and movable by said cam means between a first position when said rotatable dial prevents flow of gas and a second position, a spring biased platform movable by the other end of said crank as said crank moves between its first and second positions, said platform having an actuating pin depending therefrom and movable with said platform, said actuating pin being forced between said two spring biased pins moving said pins apart to their extended positions upon movement of said rotatable dial to open said control means and move said crank to its second position, said gas flow control units being mounted on said gas administration apparatus such that the extended pins of one gas flow unit are in alignment with the unextended pins of adjacent gas flow units and prevent the unextended pins from extending and thereby preventing opening of said control means of said other gas flow unit.

3. An anesthesia machine as defined in claim 2 wherein said locking means includes a shaft rotatable in said gas flow unit between its locked and unlocked position, said shaft further having a profiled groove, said gas-administration apparatus having a latching member adapted to engage said profiled groove, whereupon rotation of said shaft causes said latching member to move along said groove to hold said gas flow unit forcibly against said gas-administration apparatus.

4. An anesthesia machine as defined in claim 3 wherein said interlock system includes a plate rotatable with said shaft, said plate having a keying means adapted to align with keying means of said platform when said shaft is rotated to its locked position to allow movement of said platform between its first and second positions, said respective keying means further preventing movement of said platform when said shaft is in its unlocked position.

5. An anesthesia machine as defined in claim 1 comprising a plurality of gas flow units mounted on said gas-administration apparatus, said interlock means including at least one pin extending from each of said gas flow units and movable to an extended position when one of said control means is moved to its open position, said gas flow control units being mounted on said gas administration apparatus such that the extended pins of one gas flow unit are in alignment with the unextended pins of adjacent gas flow units and prevent the unextended pins from extending and thereby preventing said other control means from being moved to its open position.

6. An anesthesia machine comprising a gas-administration apparatus, including means for mounting thereon a plurality of similar gas flow units in side by side relation at least one gas flow unit removably mounted on said gas-administration apparatus in a plug-in fashion, said unit having control means to control the flow of gas to said gas flow unit from said gas-administration apparatus, gas port means in said gas-administration apparatus to conduct gas to said gas flow unit, valve means in said gas port means normally urged to closed position, locking means movable between a lock position wherein said gas flow unit is secured to said gas-administration apparatus and an unlock position, interlock means cooperating with said locking means, said control means being movable to open position to move said valve means to an open position, said interlock means preventing movement of said control means to open said valve means when said locking means is in the unlock position, said interlock means further including at least one pin depending outwardly from said gas flow unit movable to an extended position when said control means is moved to its open position to prevent the control means of a similar adjacent gas flow unit mounted on said gas-administration apparatus from being moved to its open position.

7. An anesthesia machine as defined in claim 6 wherein said interlock means comprises two intersecting spring biased pins, each extending from opposite sides of said gas flow unit and movable to an extended position against spring bias when said control means is moved to its closed position, an actuating pin movable between first and second positions by said control means when said control means is moved, respectively between its closed and open positions, said actuating pin in its first position being located a predetermined distance from the intersection of said spring biased pins, said actuating pin in its second position being forced between the intersection of said spring biased pins to force said spring biased pins apart with respect to each other to attain their extended positions, one of said extended pins thereby preventing the control means of a similar adjacent gas flow unit mounted on said gas-administration apparatus from being moved to its open position.

* * * * *